United States Patent
Matula (10) Patent No.: US 9,579,478 B2
(45) Date of Patent: Feb. 28, 2017

(54) MODULAR PATIENT INTERFACE DEVICE WITH CHAMBER AND NASAL PILLOWS ASSEMBLY

(71) Applicant: KONINKLIJKE PHILIPS N.V., Eindhoven (NL)

(72) Inventor: Jerome Matula, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 341 days.

(21) Appl. No.: 14/355,687

(22) PCT Filed: Oct. 15, 2012

(86) PCT No.: PCT/IB2012/055606
§ 371 (c)(1),
(2) Date: May 1, 2014

(87) PCT Pub. No.: WO2013/064931
PCT Pub. Date: May 10, 2013

(65) Prior Publication Data
US 2014/0299134 A1  Oct. 9, 2014

Related U.S. Application Data

(60) Provisional application No. 61/555,101, filed on Nov. 3, 2011.

(51) Int. Cl.
| | | |
|---|---|---|
| *A61M 16/06* | (2006.01) | |
| *A61M 16/00* | (2006.01) | |
| *A61M 16/08* | (2006.01) | |

(52) U.S. Cl.
CPC .... *A61M 16/0622* (2014.02); *A61M 16/0057* (2013.01); *A61M 16/06* (2013.01);
(Continued)

(58) Field of Classification Search
None
See application file for complete search history.

(56) References Cited

U.S. PATENT DOCUMENTS 5,560,354 A * 10/1996 Berthon-Jones ...... A61M 16/06
  128/204.18
6,431,172 B1   8/2002 Bordewick
(Continued)

FOREIGN PATENT DOCUMENTS

EP           634186 A2    1/1995
WO    WO2005063328 A1    7/2005
(Continued)

*Primary Examiner* — Tan-Uyen (Jackie) T Ho
*Assistant Examiner* — Joseph D Boecker
(74) *Attorney, Agent, or Firm* — Michael W. Haas (57) ABSTRACT

A patient interface device (8) includes a cushion member (10), a frame member (16), and nasal pillows (18,20). A first side (12) of the cushion member forms a seal with a patient's mouth. The nasal pillows are structured to form a seal with the patient's nares. The nasal pillows are attached to the frame member. The frame is attached to a second side (14) of the cushion member. The frame member includes a connecting portion (228), a first aperture (240), and a second aperture (242). The nasal pillows include a first nasal pillow element (218) and a second nasal pillow element (220). The first nasal pillow element is at least partially removably disposed in the first aperture. The second nasal pillow element is at least partially removably disposed in the second aperture. The connection portion is connected to the second side of the cushion member.

4 Claims, 12 Drawing Sheets

(52) U.S. Cl.
CPC .... *A61M 16/0666* (2013.01); *A61M 16/0816* (2013.01); *A61M 2210/0618* (2013.01)

(56) References Cited

U.S. PATENT DOCUMENTS

| | | |
|---|---|---|
| 2002/0096178 A1 | 7/2002 | Ziaee |
| 2006/0112962 A1* | 6/2006 | Tebbutt ............. A61M 16/0488 128/206.29 |
| 2007/0125385 A1* | 6/2007 | Ho ........................ A61M 16/06 128/206.26 |
| 2009/0277452 A1 | 11/2009 | Lubke |
| 2010/0132717 A1* | 6/2010 | Davidson .............. A61M 16/06 128/207.18 |
| 2011/0056497 A1 | 3/2011 | Scheiner |
| 2011/0315143 A1* | 12/2011 | Frater ................... A61M 16/06 128/205.24 |
| 2013/0199537 A1* | 8/2013 | Formica ................ A61M 16/06 128/205.25 |

FOREIGN PATENT DOCUMENTS

| | | |
|---|---|---|
| WO | WO2007130067 A1 | 11/2007 |
| WO | WO2007139531 A1 | 12/2007 |

* cited by examiner

MODULAR PATIENT INTERFACE DEVICE WITH CHAMBER AND NASAL PILLOWS ASSEMBLY

CROSS-REFERENCE TO RELATED APPLICATIONS

This patent application claims the priority benefit under 35 U.S.C. §371 of international patent application no. PCT/IB2012/055606, filed Oct. 15, 2012, which claims the priority benefit under 35 U.S.C. §119(e) of U.S. Provisional Application No. 61/555,101 filed on Nov. 3, 2011, the contents of which are herein incorporated by reference.

BACKGROUND OF THE INVENTION

1. Field of the Invention

The present invention relates to respiratory patient interface systems, and, in particular, to a respiratory patient interface device including a modular frame member and dual chamber nasal pillows assembly.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver continuous positive airway pressure (CPAP) or variable airway pressure, which varies with the patient's respiratory cycle, to treat a medical disorder, such as sleep apnea syndrome, in particular, obstructive sleep apnea (OSA), or congestive heart failure.

Non-invasive ventilation and pressure support therapies involve the placement of a patient interface device including a mask component on the face of a patient. The mask component may be, without limitation, a nasal mask that covers the patient's nose, a nasal cushion that rests beneath the patient's nose (such as a "pillows" style nasal cushion having nasal prongs that are received within the patient's nares or a "cradle" style nasal cushion that rests beneath and covers the patient's nares), a nasal/oral mask that covers the nose and mouth, or a full face mask that covers the patient's face. The patient interface device interfaces the ventilator or pressure support device with the airway of the patient through tubing, so that a flow of breathing gas can be delivered from the pressure/flow generating device to the airway of the patient. It is known to maintain such devices on the face of a wearer by a headgear having one or more straps adapted to fit over/around the patient's head.

Patient interface devices that have a mouth cushion and nasal pillows, for example, are typically constructed with the pillows forming a part of the mouth cushion. Accordingly, the flow of gas generated by the ventilator or pressure support device enters into a single chamber. In other words, there is no way to effectively and efficiently customize the patient interface device, for example, by allowing various sizes and combinations of pillows and/or mouth cushions to be installed and employed to provide a customized, enhanced fit for the patient.

SUMMARY OF THE INVENTION

Accordingly, it is an object of the present invention to provide a patient interface device that overcomes the shortcomings of conventional patient interface devices. This object is achieved according to one embodiment of the invention by providing a patient interface device having a modular frame member and dual chamber nasal pillows assembly.

It is yet another object of the present invention to provide a method of delivering a flow of breathing gas that does not suffer from the disadvantages associated with conventional techniques. This object is achieved by providing a method that includes delivering a flow of breathing gas through a dual chamber pillows assembly of a patient interface device.

In one embodiment, a patient interface device, comprises a cushion member including a first side structured to form a seal with a patient's mouth, and a second side disposed opposite the first side; a frame member; and nasal pillows structured to form a seal with the patient's nares. The nasal pillows are attached to the frame member. The frame is attached to the second side of the cushion member.

The frame member includes a connecting portion, a first aperture, and a second aperture. The nasal pillows include a first nasal pillow element and a second nasal pillow element. The first nasal pillow element is structured to be at least partially removably disposed in the first aperture, and the second nasal pillow element is structured to be at least partially removably disposed in the second aperture. The connection portion is connected to the second side of the cushion member. The frame member further includes a first molded chamber and a second molded chamber. The first molded chamber is in fluid communication with the first aperture and the first nasal pillow element, and the second molded chamber is in fluid communication with the second aperture and the second nasal pillow element.

In another embodiment, a method of delivering a flow of breathing gas to a patient is provided that includes generating the flow of breathing gas; and delivering the flow of breathing gas to a patient interface device. The patient interface device includes a cushion member, a frame member, and nasal pillows. The cushion member includes a first side structured to form a seal with a patient's mouth, and a second side disposed opposite the first side. The nasal pillows are structured to form a seal with the patient's nares. The nasal pillows are attached to the frame member, and the frame is attached to the second side of the cushion member.

These and other objects, features, and characteristics of the invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "connected," "attached" and "directly coupled" mean that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
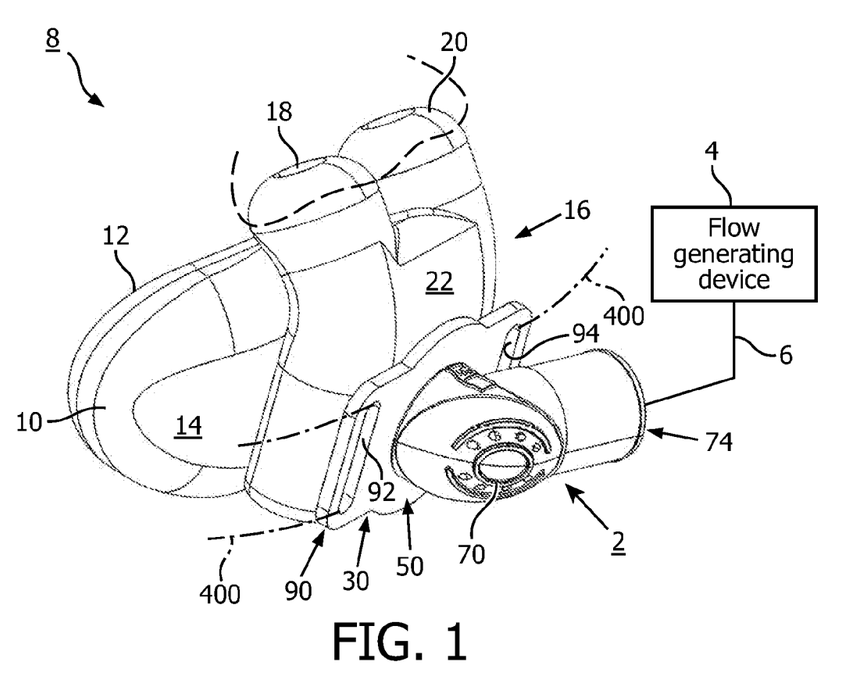
FIG. 1 is a simplified view of a system adapted to provide a regimen of respiratory therapy to a patient according to one exemplary embodiment of the invention.
Figure 2:
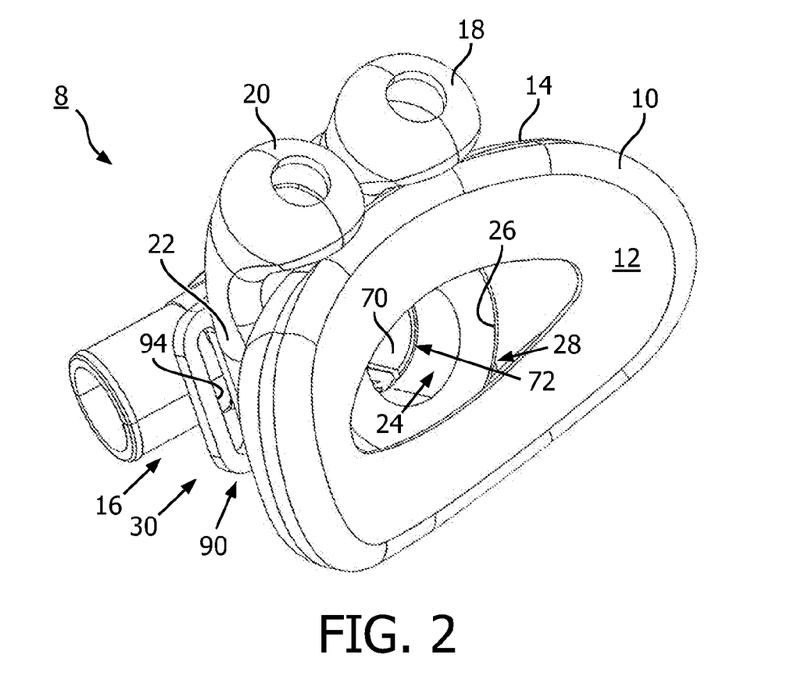
FIG. 2 is a back isometric view of a patient interface device forming a part of the system of FIG. 1.

A system 2 adapted to provide a regimen of respiratory therapy to a patient according to one exemplary embodiment is generally shown in FIG. 1. System 2 includes a flow generating device 4, a delivery conduit 6, and a patient interface device 8. Flow generating device 4 is structured to generate a flow of breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pa.), and auto-titration pressure support devices. Conduit 6 is structured to communicate the flow of breathing gas from flow generating device 4 to patient interface device 8 through conduit 6. Conduit 6 and patient interface device 8 are often collectively referred to as a patient circuit.

In FIGS. 1-5, patient interface device 8, in accordance with one non-limiting exemplary embodiment of the invention, includes a cushion member 10 having first and second opposing sides 12,14. First side 12 is structured to form a seal with a patient's mouth (not shown). A frame member 16 (best shown in the exploded view of FIG. 3) is attached to second side 14 of cushion member 10. Nasal pillows 18,20, which are structured to form a seal with the patient's nares (partially shown in phantom line drawing in FIG. 1), are attached to frame member 16, as will be described in further detail herein.

In the example of FIGS. 1-5, a single piece unitary molded member is formed to include a first nasal pillow element 18 and a second nasal pillow element 20. The single piece unitary molded member further includes a body portion 22 with an exterior, an interior, a molded chamber 24 formed on the interior, and a through hole 26 (best shown in FIG. 3). Through hole 26 extends through body portion 22.

Figure 3:
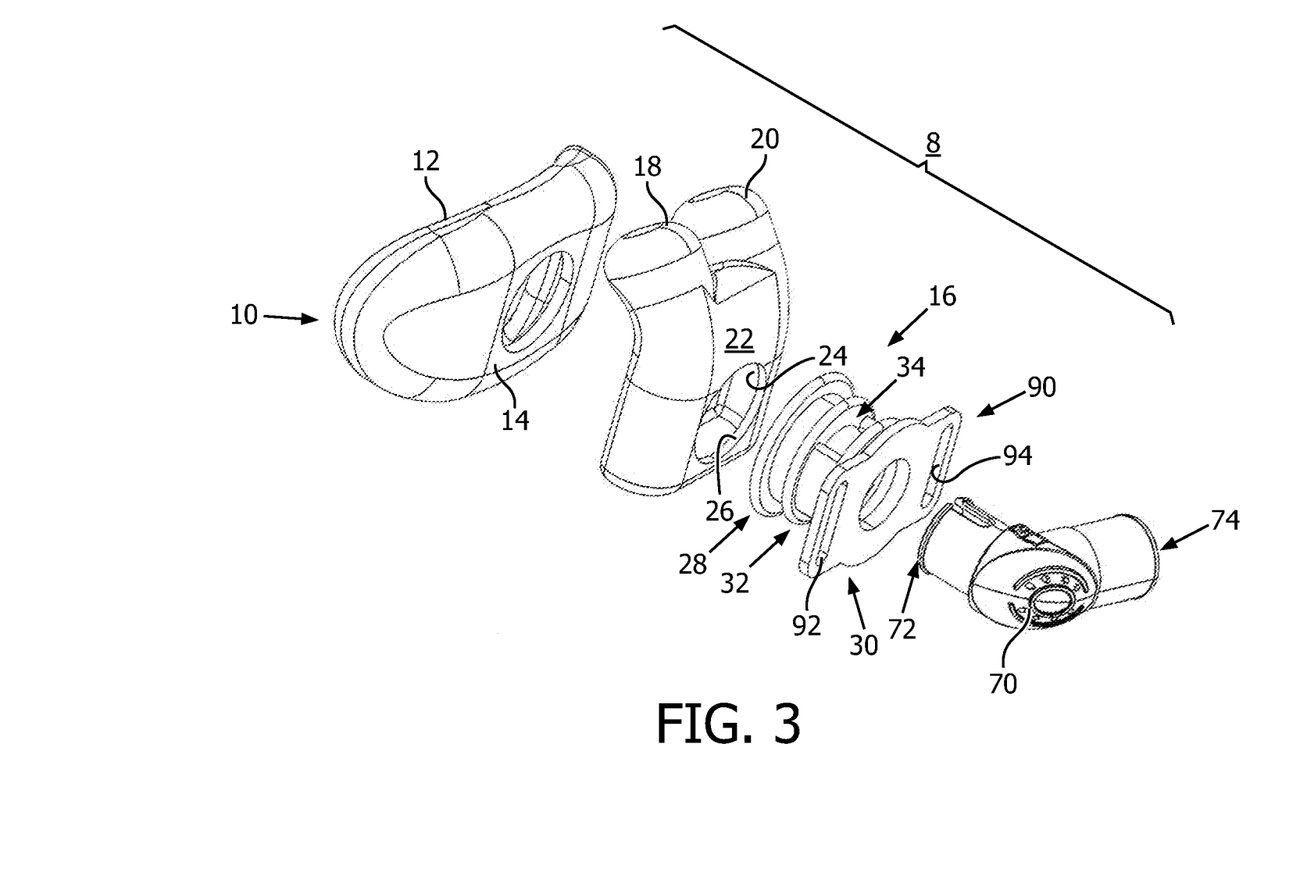
FIG. 3 is an exploded view of the patient interface device of FIG. 2.
Figure 4:
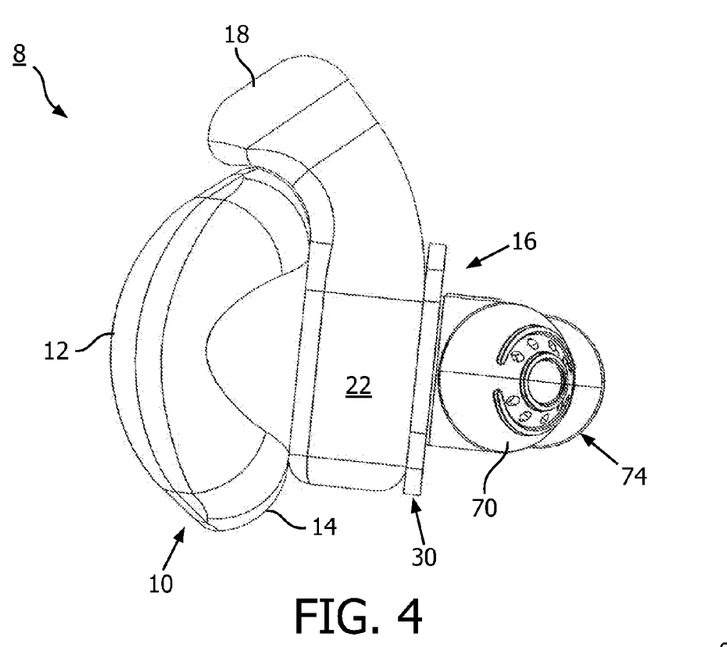
FIG. 4 is a side elevation view of the patient interface device of FIG. 2.
Figure 5:
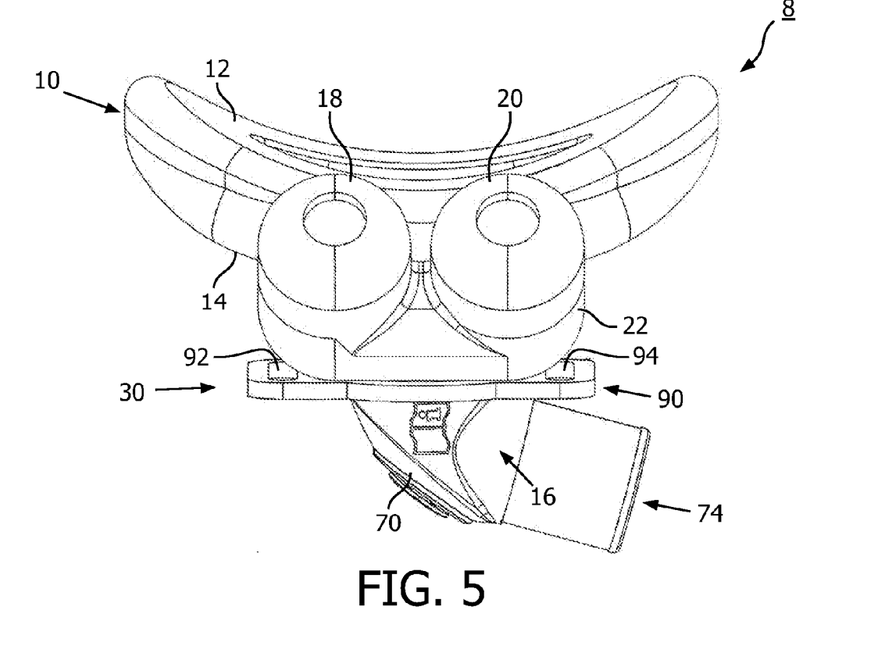
FIG. 5 is a top elevation view of the patient interface device of FIG. 2.
Figure 6:
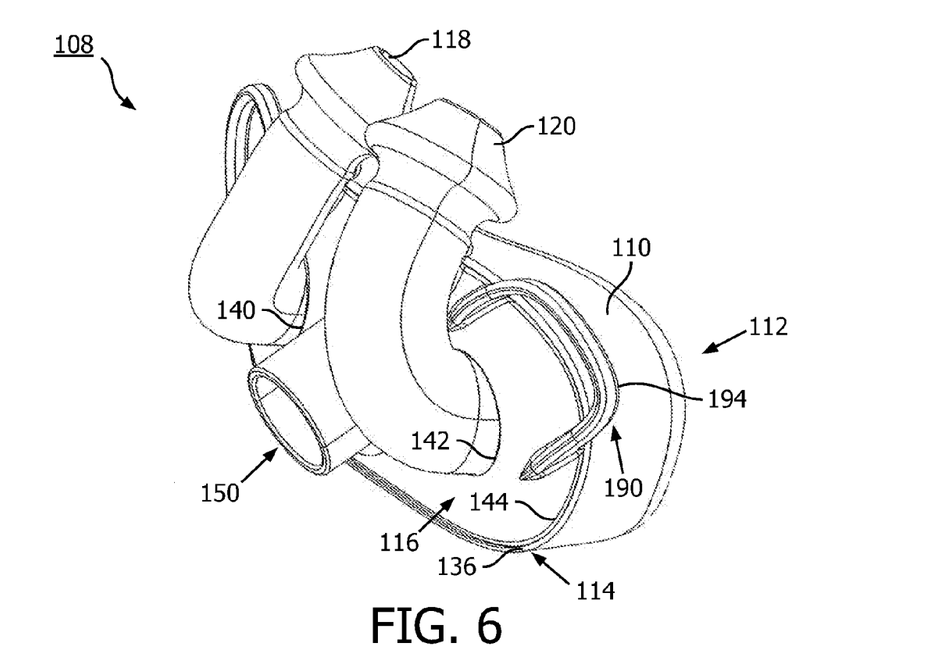
FIG. 6 is a front isometric view of a patient interface device in accordance with another exemplary embodiment of the invention.
Figure 7:
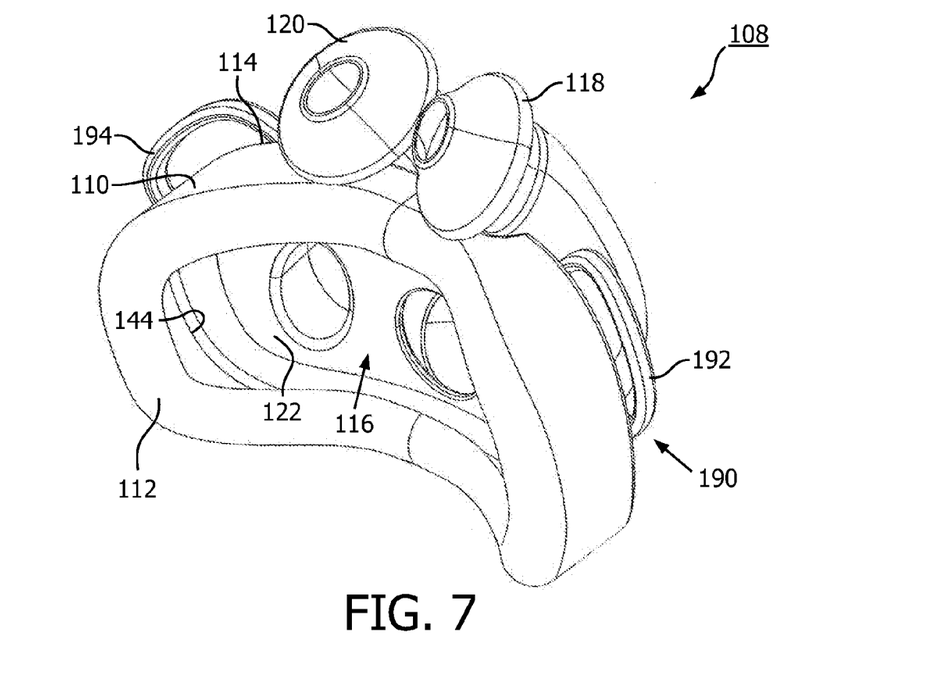
FIG. 7 is a back isometric view of a patient interface device of FIG. 6.
Figure 8:
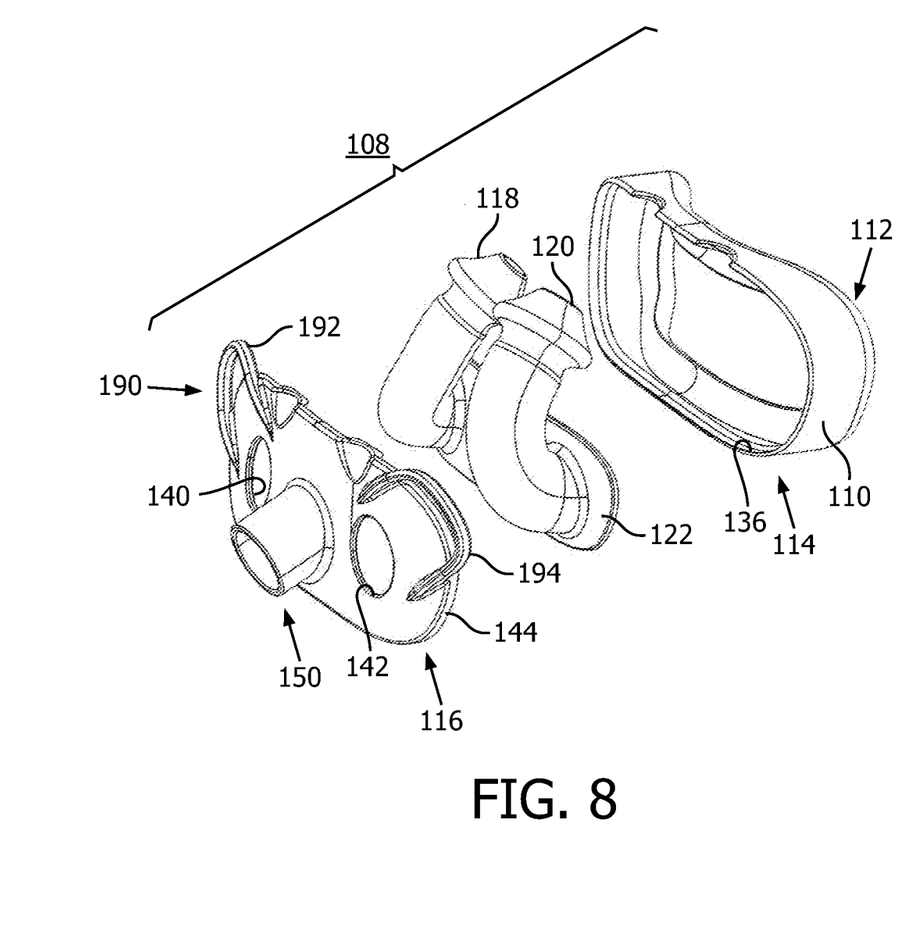
FIG. 8 is an exploded view of the patient interface device of FIG. 7.
Figure 9:
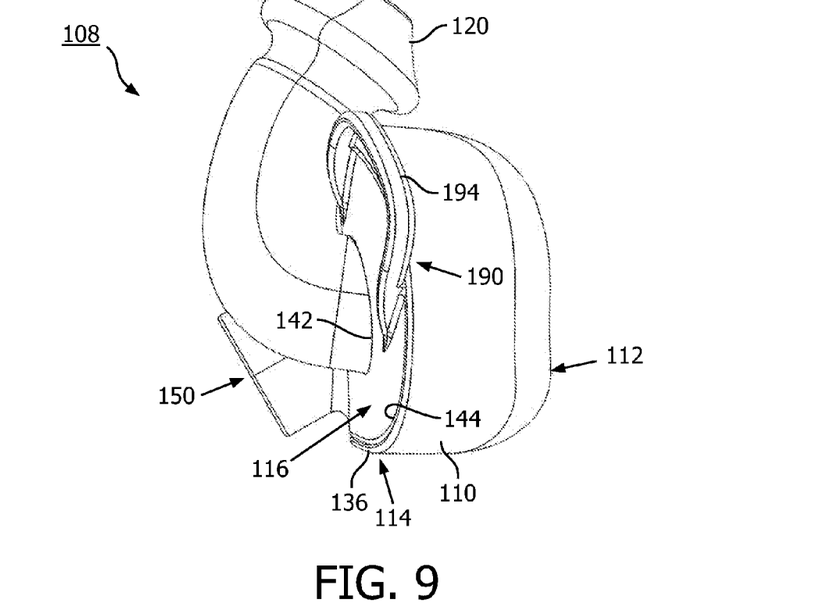
FIG. 9 is a side elevation view of the patient interface device of FIG. 7.
Figure 10:
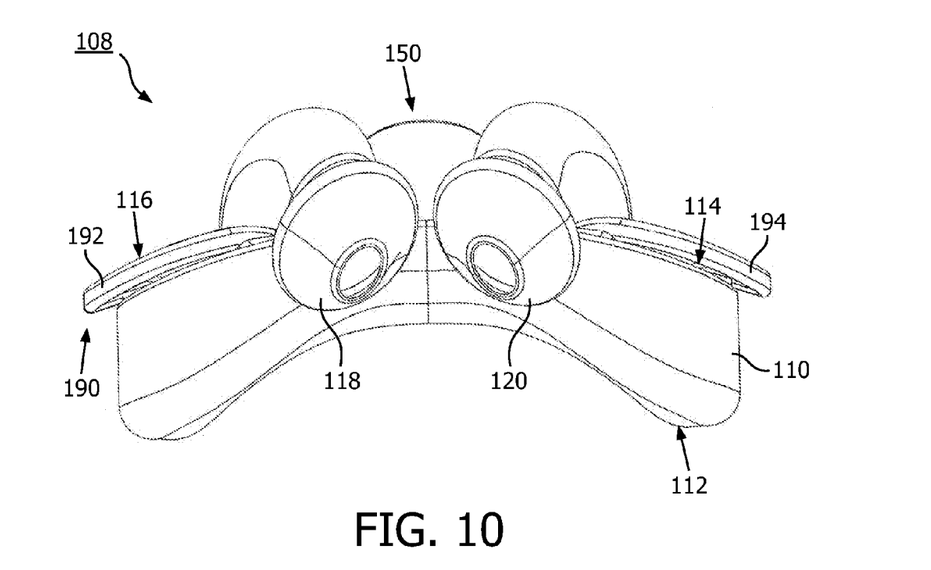
FIG. 10 is a top elevation view of the patient interface device of FIG. 7.
Figure 11:
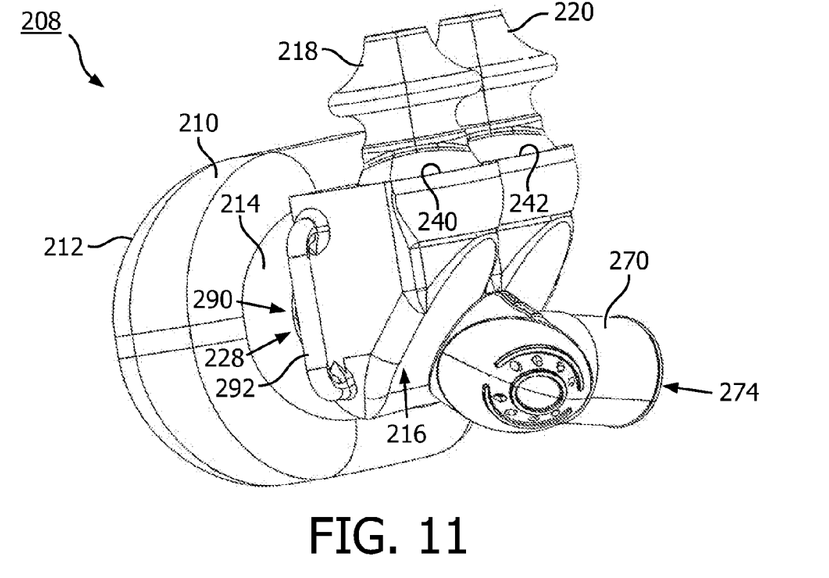
FIG. 11 is a front isometric view of a patient interface device in accordance with another exemplary embodiment of the invention.

As shown in FIG. 3, frame member 16 has an inlet end 28, an outlet end 30, and an intermediate portion 32 extending therebetween. Intermediate portion 32 includes an air channel 34. When patient interface device 8 is assembled, inlet end 28 extends through through hole 26 and connects frame member 16 to second side 14 of cushion member 10. Intermediate portion 32 is then disposed within molded chamber 24, in order that air channel 34 is in fluid communication with first nasal pillow element 18, second nasal pillow element 20, and cushion member 10. Outlet end 30 of frame member 16 is structured to receive a fluid coupling member on the exterior of body portion 22. In FIGS. 1-5, fluid coupling member 70 is an elbow, although it will be appreciated that any known or suitable alternative fluid coupling member (not shown) could be employed within the scope of the invention.

Exemplary elbow 70 includes inlet end 72 and outlet end 74, as shown in FIG. 3. Inlet end 72 is structured to be coupled to a fluid coupling portion 50 of frame member 16. Specifically, inlet end 72 of elbow 70 is inserted through fluid coupling portion 50, which in the non-limiting example of FIGS. 1-5 is an opening extending through frame member 16. Outlet end 74 of elbow 70 is structured to be connected to aforementioned conduit 6 (shown in simplified form in FIG. 1) for delivering a flow of breathing gas to the patient.

Continuing to refer to FIG. 1, exemplary frame member 16 further includes an attachment portion 90, which in the example shown and described with respect to FIGS. 1-5, comprises a pair of elongated slots 92,94 (both shown in FIGS. 1, 3 and 5) structured to attach patient interface device 8 to a suitable headgear assembly 400 (partially shown in simplified form in phantom line drawing in FIG. 1). In this manner, frame member 16 and, in particular, headgear assembly 400 attached thereto, may be employed to secure patient interface device 8 to the patient's face in the desired orientation.

FIGS. 6-10 illustrate another non-limiting example embodiment of a patient interface device 108, in accordance with the present invention. Like aforementioned patient interface device 8, discussed hereinabove with reference to FIGS. 1-5, patient interface device 108 includes a cushion member 110 having first and second opposing sides 112,114, a frame member 116, and nasal pillows 118,120. As best shown in the exploded view of FIG. 8, preferably a single piece unitary molded member has a base flange 122 and first and second nasal pillow elements 118,120 separately extending outwardly from base flange 122. Frame member 116 includes an interior, an exterior, a first aperture 140, a second aperture 142, a peripheral edge 144, and a fluid coupling portion 150. Fluid coupling portion 150, in the example of FIGS. 6-10, forms a molded conduit extending from the exterior of frame member 116 to the interior of frame member 116.

When patient interface device 108 is assembled, first nasal pillow element 118 extends through first aperture 140, and second nasal pillow element 120 extends through second aperture 142, and base flange 122 is disposed between the interior of frame member 116 and cushion member 110. A peripheral lip 136 on second side 114 of cushion member 110 at least partially overlays peripheral edge 144 of frame member 116 to connect frame member 116 to cushion member 110, as shown for example in FIG. 6.

Patient interface device 108 also includes an attachment portion 190, which in the non-limiting example shown and described with respect to FIGS. 6-10, comprises first and second molded loops 192,194 to which the aforementioned headgear assembly 400 (shown and previously described with respect to FIG. 1), for example and without limitation, can be attached.

FIGS. 11-15 show another non-limiting example embodiment of a patient interface device 208, in accordance with the present invention. Patient interface device 208 includes a cushion member 210 having first and second opposing sides 212,214, a frame member 216 attached to second side 214 of cushion member 210, and nasal pillows 218,220 attached to frame member 216.

Frame member 216 further includes a connecting portion 228 connected to second side 214 of cushion member 210, a first aperture 240, and a second aperture 242 (both shown in FIGS. 11-13 and 15). The nasal pillows in the example of FIGS. 11-15, comprise a first nasal pillow element 218 and a second nasal pillow element 220. First nasal pillow element 218 is structured to be at least partially removably disposed in first aperture 240, and second nasal pillow element 220 is structured to be at least partially removably disposed in second aperture 242.

Figure 12:
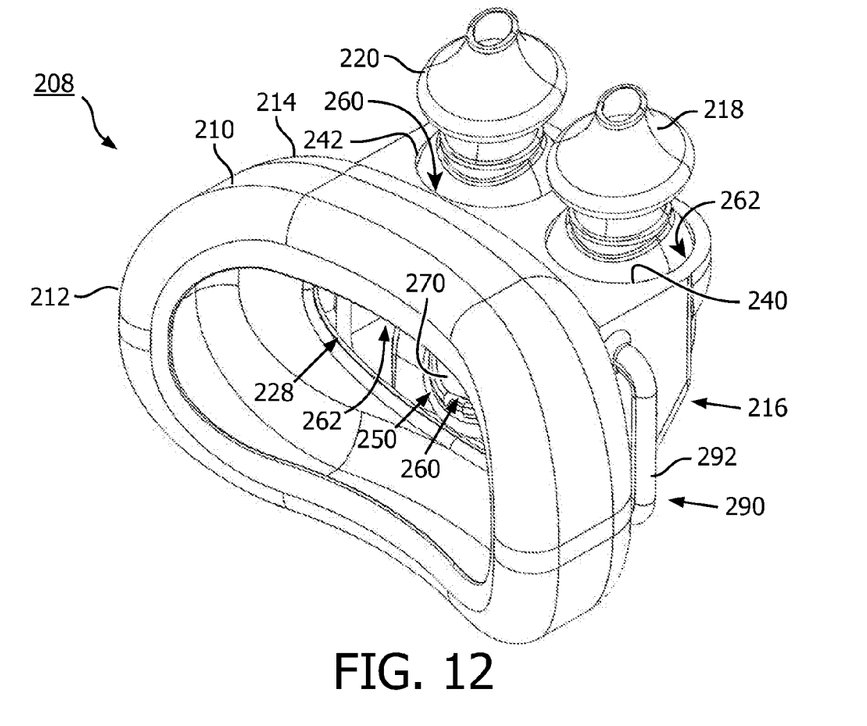
FIG. 12 is a back isometric view of a patient interface of FIG. 11.
Figure 13:
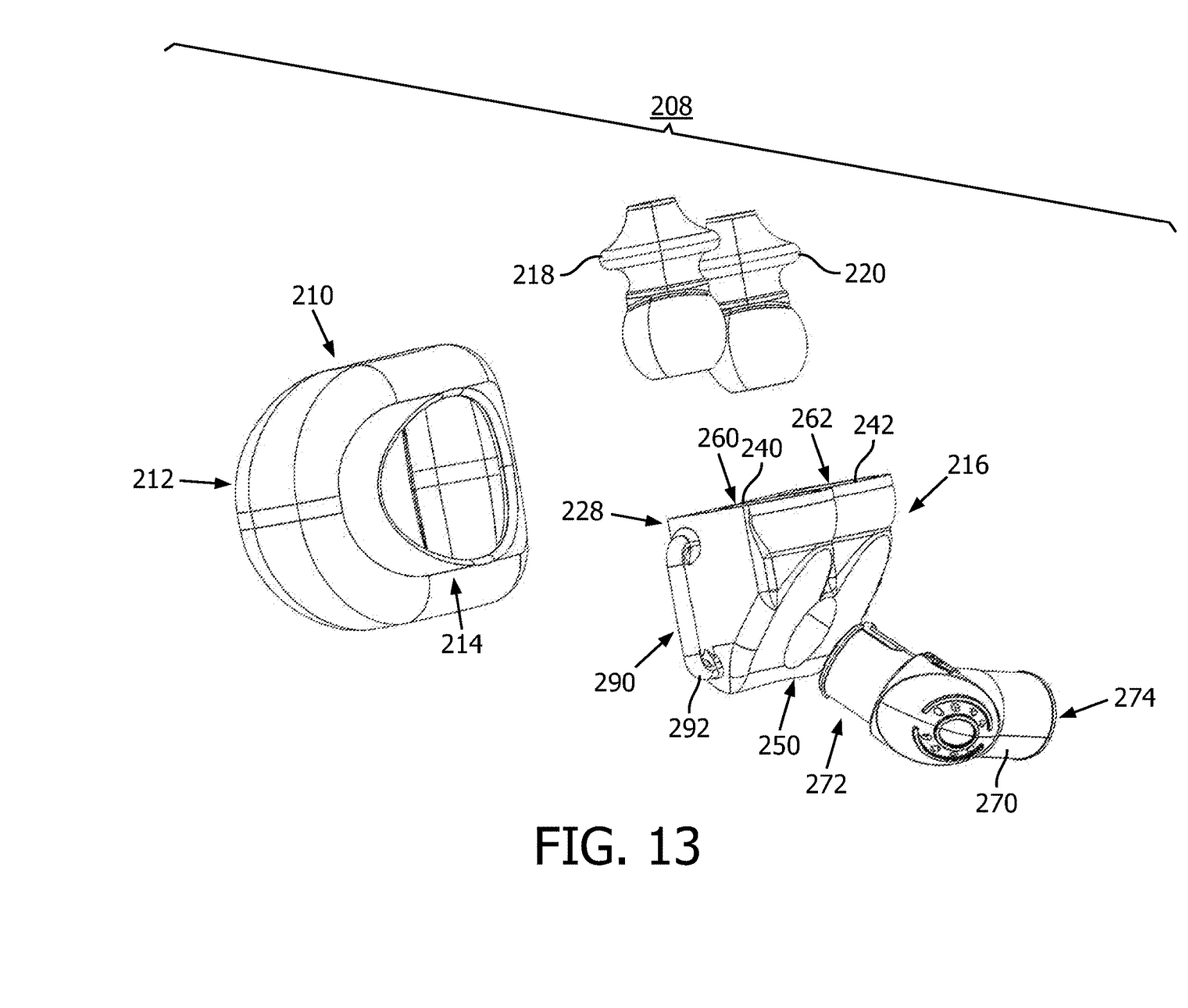
FIG. 13 is an exploded view of the patient interface device of FIG. 11.
Figure 14:
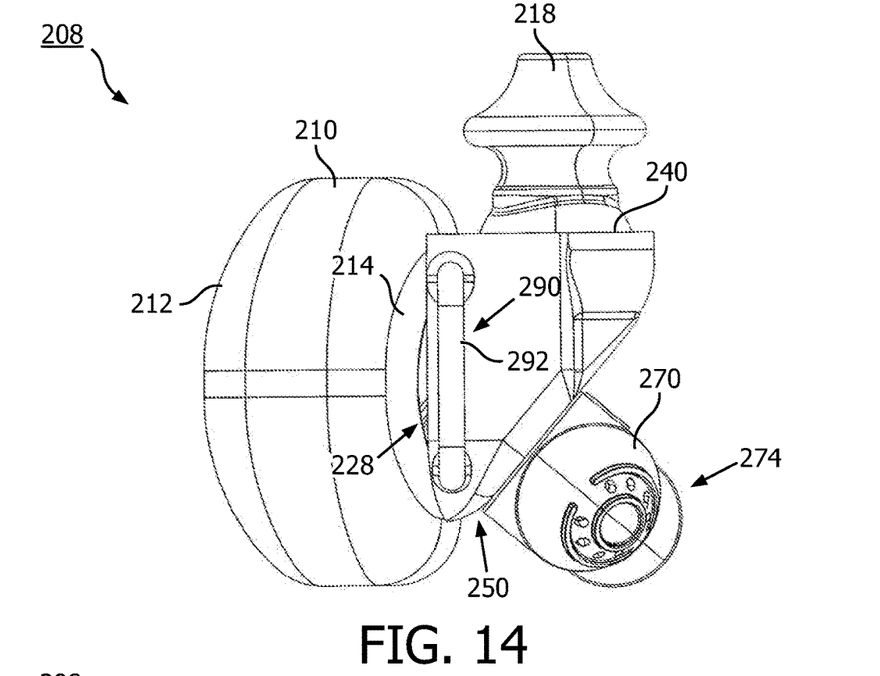
FIG. 14 is a side elevation view of the patient interface device of FIG. 11.
Figure 15:
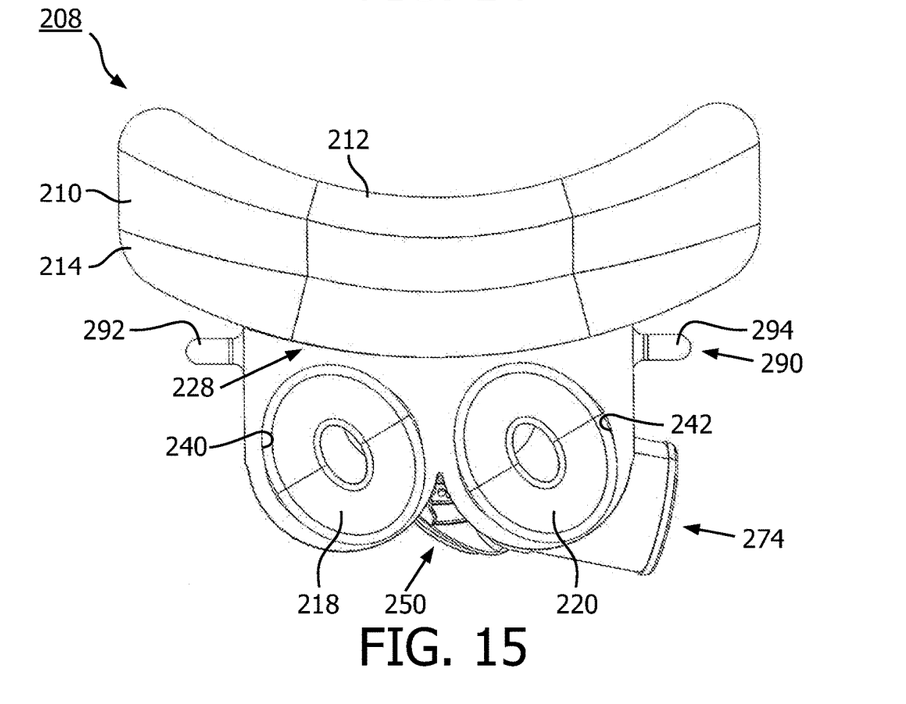
FIG. 15 is atop elevation view of the patient interface device of FIG. 11.
Figure 16:
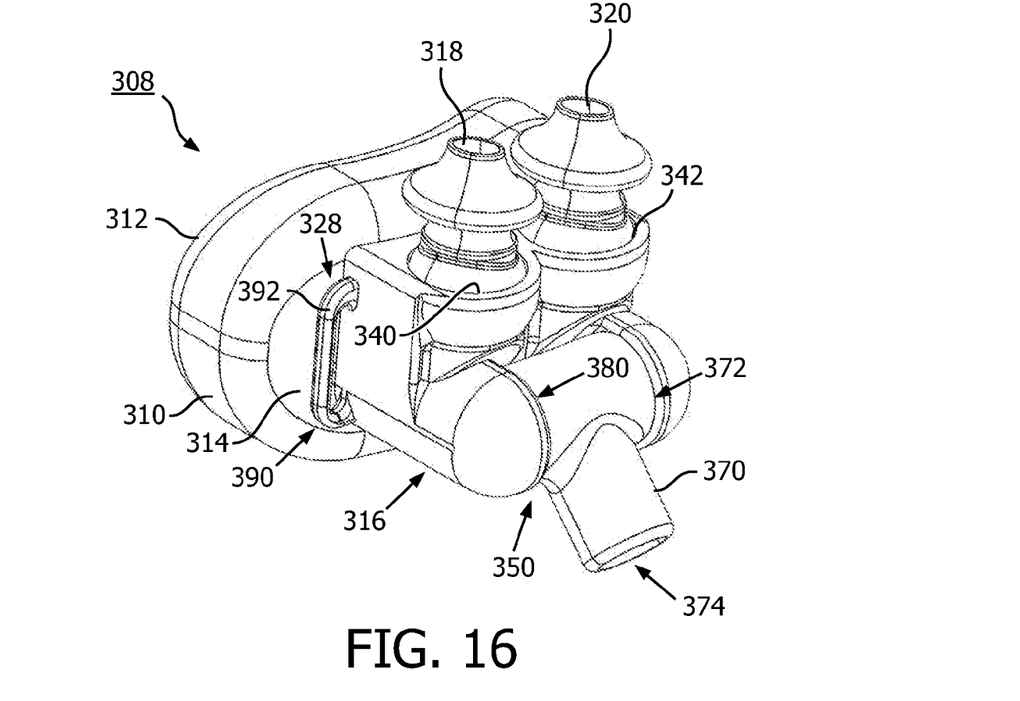
FIG. 16 is a front isometric view of a patient interface device in accordance with another exemplary embodiment of the invention.
Figure 17:
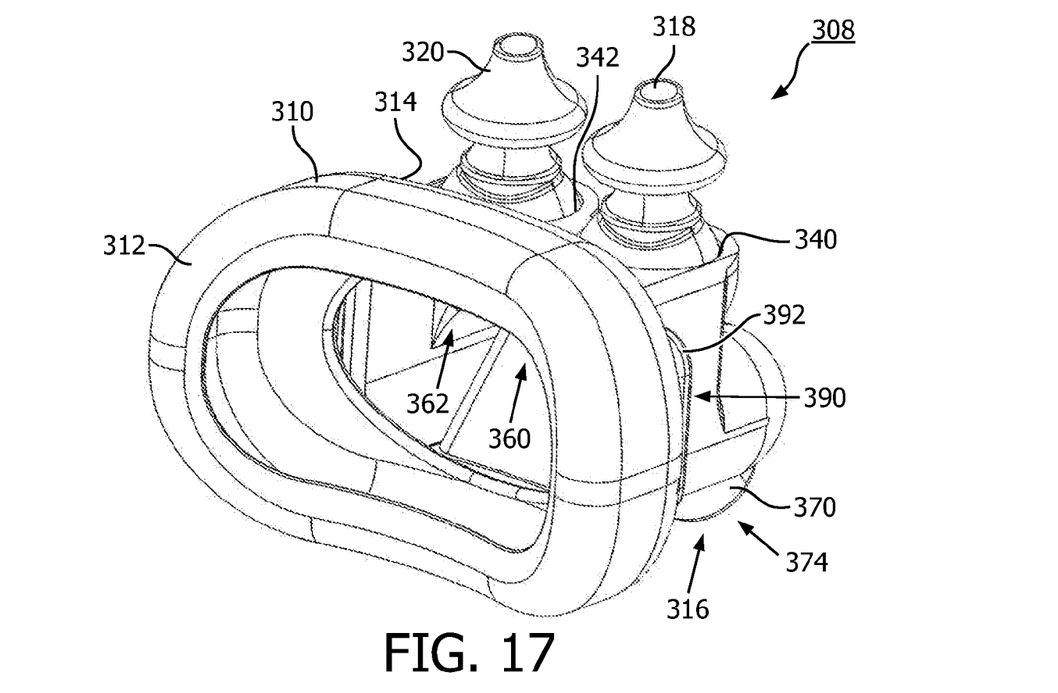
FIG. 17 is a back isometric view of a patient interface device of FIG. 16.

As shown in FIGS. 12 and 13, frame member 216 further includes a first molded chamber 260 and a second molded chamber 262. First molded chamber 260 is in fluid communication with first aperture 240 and first nasal pillow element 218. Second molded chamber 262 is in fluid communication with second aperture 242 and second nasal pillow element 220. Frame member 216 of patient interface device 208 further includes a fluid coupling portion 250, which in the example shown is a hole extending through frame member 216. Fluid coupling portion 250 is structured to receive an inlet end 272 of a fluid coupling member 270 such as, for example and without limitation, the elbow shown. As previously discussed, elbow 270 also includes an outlet end 274, which is structured to be coupled, for example and without limitation, to aforementioned conduit 6 (shown and described with respect to FIG. 1).

Frame member 216 further includes attachment portion 290, which in the non-limiting example of FIGS. 11-15, is a pair of molded members 292,294 (both shown in FIG. 15), to which a suitable headgear assembly 400 (shown and described hereinabove with respect to FIG. 1), for example and without limitation, is attached.

FIGS. 16-20 show a different, non-limiting example embodiment of a patient interface device 308, in accordance with the instant invention. Patient interface device 308 includes a cushion member 310 having first and second opposing sides 312,314, a frame member 316 attached to second side 314 of cushion member 310, and nasal pillows 318,320 attached to frame member 316. More specifically, as will be appreciated with reference to the exploded view of FIG. 18, frame member 316 includes a connection portion 328 for connecting frame member 316 and nasal pillow elements 318,320 to cushion member 310 (also shown in the back isometric view of FIG. 17).

Frame member 316 further includes first and second apertures 340,342 forming first and second molded chambers 360,362 (FIGS. 17 and 18) for removably receiving at least a portion of first and second nasal pillow elements 318,320, respectively. Accordingly, first molded chamber 360 is in fluid communication with first aperture 340 and first nasal pillow element 318, and second molded chamber 362 is in fluid communication with second aperture 342 and second nasal pillow element 320.

Figure 18:
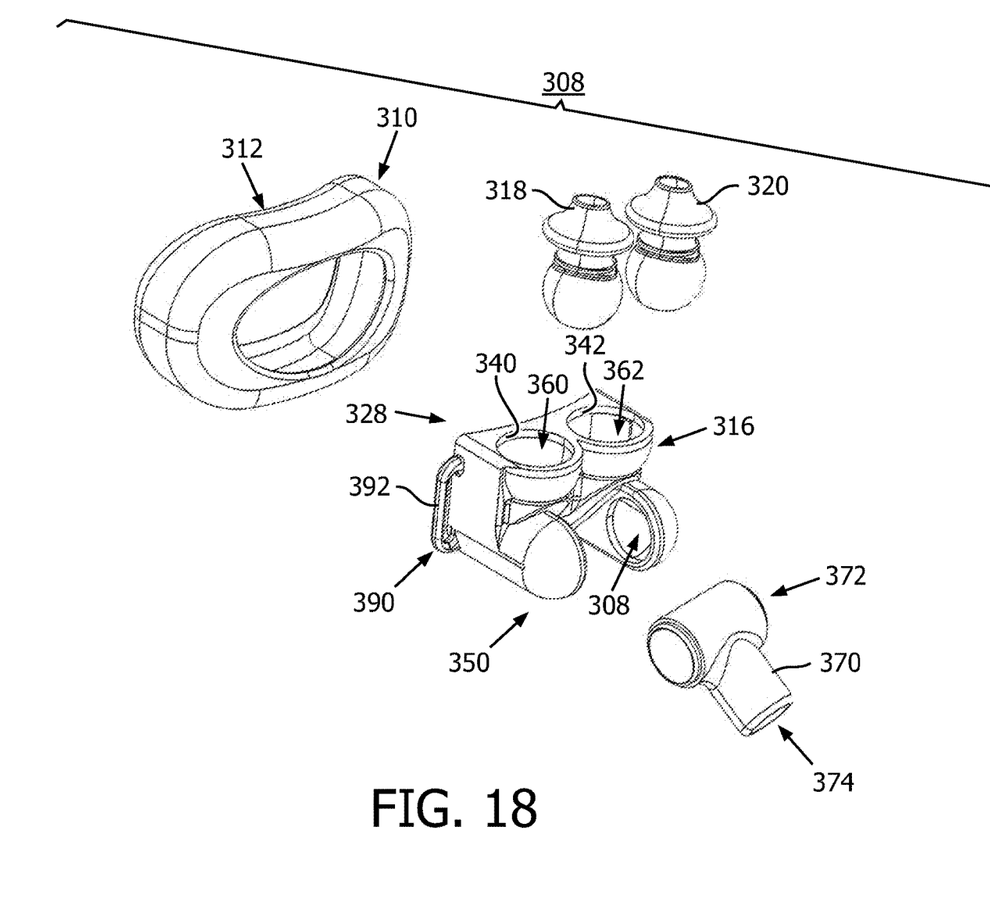
FIG. 18 is an exploded view of the patient interface device of FIG. 16.
Figure 19:
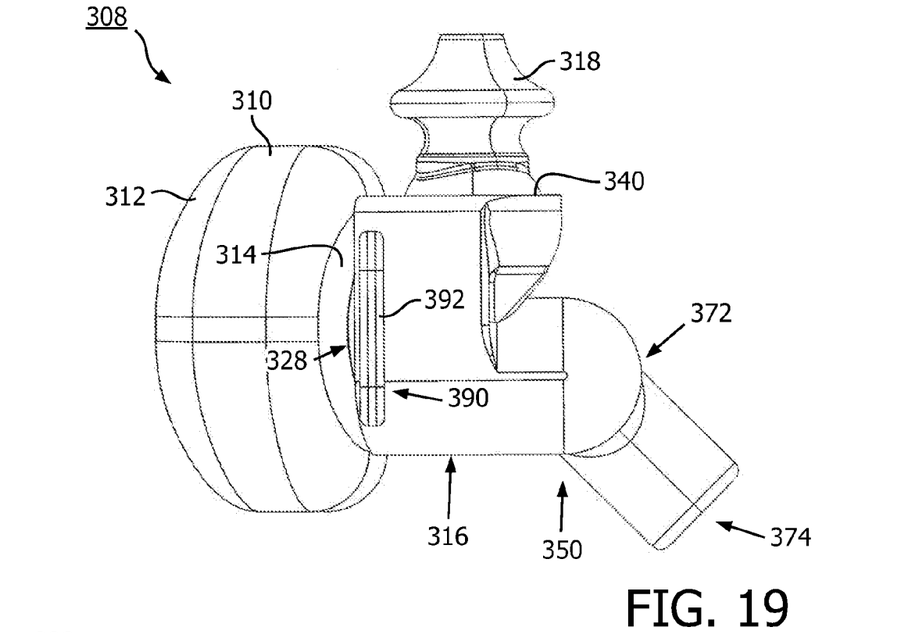
FIG. 19 is a side elevation view of the patient interface device of FIG. 16.
Figure 20:
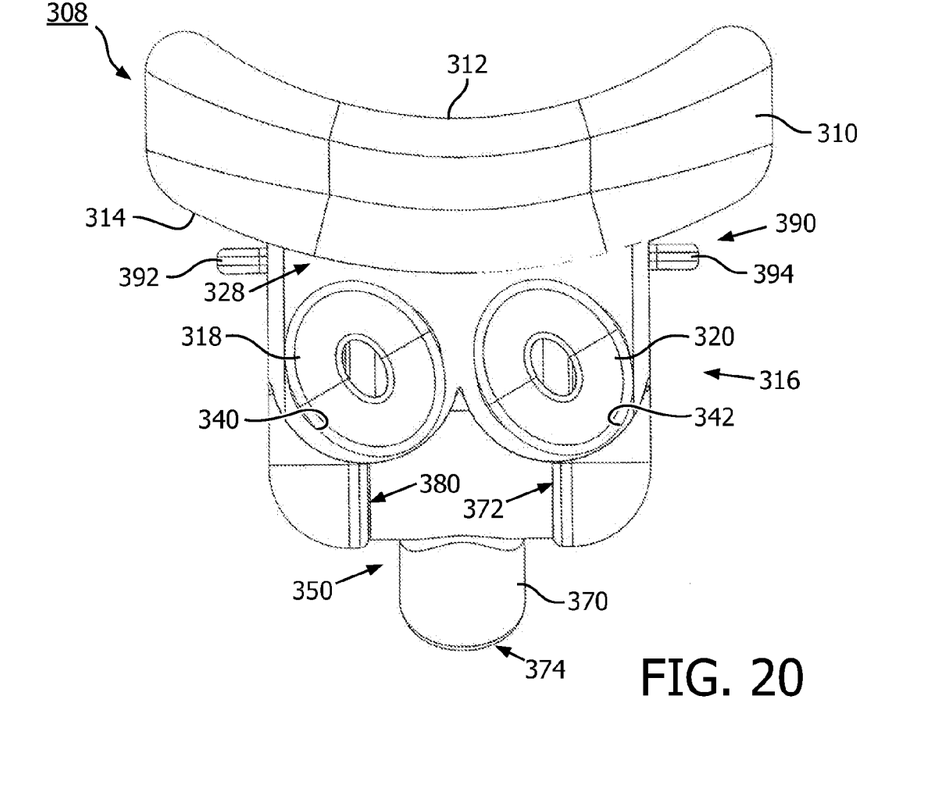
FIG. 20 is a top elevation view of the patient interface device of FIG. 16.

In the example of FIGS. 16-20, frame member 316 also has a fluid coupling portion 350, which comprises a molded socket 380 (best shown in FIG. 18). A fluid coupling member 370, which in the example shown and described is a T-fitting, includes an inlet end 372 pivotably disposed in molded socket 380, as shown for example in FIG. 16. An outlet end 374 of T-fitting 370 is connectable, for example, to aforementioned conduit 6 (shown and described with respect to FIG. 1).

Frame member 316 also includes an attachment portion 390, which in the non-limiting example of FIGS. 16-20 is a pair of molded members 392,294 (both shown in FIG. 20) structured to be employed, for example and without limitation, to a suitable headgear assembly 400 (shown and described hereinabove with respect to FIG. 1) for securing patient interface device 308 to the patient's face in the desired orientation.

Accordingly, among other benefits, the invention provides an improved patient interface device 8,108,208,308, which has a modular design allowing for various combinations of types, sizes and/or configurations of components to be installed onto a separate frame member (e.g., without limitation, 16, 116, 216, 316) to provide a customized fit. That is, nasal pillow elements (e.g., without limitation, 18, 20, 118, 120, 218, 220, 318, 320) are separate from mouth cushion member (e.g., without limitation, 10, 110, 210, 310) and are coupled together with a dual chamber frame member (e.g., without limitation, 16, 116, 216, 316).

It can thus be appreciated that the present invention provides a patient interface device having a frame member and nasal pillows assembly that is separate from the mouth cushion member, thereby providing dual chamber pillows and allowing the assembly to be custom tailored to the patient.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A patient interface device, comprising:
a cushion member including a first side structured to form a seal with a patient's mouth, and a second side disposed opposite the first side;
a frame member having an inlet end, an outlet end, and an intermediate portion extending between the inlet end and the outlet end; and
nasal pillows structured to form a seal with the patient's nares,
wherein the nasal pillows are attached to the frame member,
wherein the frame member is attached to the second side of the cushion member,
wherein the nasal pillows comprise a single piece unitary molded member having a first nasal pillow element and a second nasal pillow element,
wherein the molded member has a body portion with an exterior, an interior, a molded chamber formed on the interior, and a through hole extending through the body portion,
wherein the intermediate portion of the frame member includes an air channel,
wherein the inlet end of the frame member extends through the through hole of the molded member and connects the frame member to the second side of the cushion member,
wherein the intermediate portion of the frame member is disposed within the molded chamber of the molded member in order that the air channel is in fluid communication with the first nasal pillow element, the second nasal pillow element, and the cushion member, and
wherein the outlet end of the frame member is structured to receive a fluid coupling member on the exterior of the body portion.

2. The patient interface device of claim 1, wherein the frame member includes an attachment portion structured to be attached to a head gear for securing the patient interface device to the patient's face.

3. A method of delivering a flow of breathing gas to a patient, comprising:

generating the flow of breathing gas; and
delivering the flow of breathing gas to a patient interface device, the patient interface device including:
a cushion member including a first side structured to form a seal with the patient's mouth, and a second side disposed opposite the first side,
a frame member having an inlet end, an outlet end, and an intermediate portion extending between the inlet end and the outlet end, and
nasal pillows attached to the frame member the nasal pillows being structured to form a seal with the patient's nares,
wherein the nasal pillows are attached to the frame member,
wherein the frame member is attached to the second side of the cushion member,
wherein the nasal pillows comprise a single piece unitary molded member having a first nasal pillow element and a second nasal pillow element,
wherein the single piece unitary molded member has a body portion with an exterior, an interior, a molded chamber formed on the interior, and a through hole extending through the body portion,
wherein the intermediate portion includes an air channel,
wherein the inlet end extends through the through hole and connects the frame member to the second side of the cushion member,
wherein the intermediate portion is disposed within the molded chamber in order that the air channel is in fluid communication with the first nasal pillow element, the second nasal pillow element, and the cushion member, and
wherein the outlet end is structured to receive a fluid coupling member on the exterior of the body portion.

4. A patient interface device, comprising:
a cushion member including a first side structured to form a seal with a patient's mouth, and a second side disposed opposite the first side;
a frame member having an inlet end, an outlet end, and an intermediate portion extending between the inlet end and the outlet end, the outlet end being attached to the second side of the cushion member; and
a molded member having a body portion with an exterior, an interior, a molded chamber formed on the interior, and a through hole extending through the body portion, the molded member further including a first nasal pillow element in fluid communication with the molded chamber and a second nasal pillow element in fluid communication with the molded chamber,
wherein the intermediate portion of the frame member includes an air channel,
wherein the intermediate portion of the frame member is disposed within the through hole of the molded member such that the air channel of the frame member is in fluid communication with the molded chamber of the molded member, and
wherein the outlet end of the frame member is structured to receive a fluid coupling member on the exterior of the body portion.

* * * * *